United States Patent
Chien

(10) Patent No.: US 10,772,520 B2
(45) Date of Patent: Sep. 15, 2020

(54) INTRAOPERATIVE MAGNETOMETRY MONITORING SYSTEM

(71) Applicant: DePuy Synthes Products, Inc., Raynham, MA (US)

(72) Inventor: Dennis Chien, West Chester, PA (US)

(73) Assignee: DEPUY SYNTHES PRODUCTS, INC., Rayntham, MA (US)

( * ) Notice: Subject to any disclaimer, the term of this patent is extended or adjusted under 35 U.S.C. 154(b) by 858 days.

(21) Appl. No.: 14/749,804

(22) Filed: Jun. 25, 2015

(65) Prior Publication Data
US 2016/0374579 A1    Dec. 29, 2016

(51) Int. Cl.
  A61B 5/04    (2006.01)
  A61B 5/00    (2006.01)

(52) U.S. Cl.
CPC ........ *A61B 5/04005* (2013.01); *A61B 5/0004* (2013.01); *A61B 5/04001* (2013.01); *A61B 5/4041* (2013.01); *A61B 5/6847* (2013.01); *A61B 5/6877* (2013.01); *A61B 5/742* (2013.01)

(58) Field of Classification Search
CPC ................................................ A61B 5/04005
See application file for complete search history.

(56) References Cited

U.S. PATENT DOCUMENTS

| 7,177,677 B2 | 2/2007 | Kaula et al. |
| 8,583,208 B2 | 11/2013 | Adachi et al. |
| 2002/0115571 A1 | 8/2002 | Yokosawa et al. |
| 2006/0091881 A1* | 5/2006 | Clarke .................. G01R 33/326 324/301 |
| 2007/0085534 A1 | 4/2007 | Seki et al. |
| 2008/0084204 A1 | 4/2008 | Seki et al. |
| 2010/0036384 A1* | 2/2010 | Gorek .................... A61B 34/20 606/104 |
| 2010/0168561 A1 | 7/2010 | Anderson |
| 2010/0327862 A1 | 12/2010 | Nagasaka |
| 2014/0012133 A1 | 1/2014 | Sverdlik et al. |
| 2014/0073903 A1 | 3/2014 | Weber et al. |

(Continued)

FOREIGN PATENT DOCUMENTS

| EP | 0 492 263 | 7/1992 |
| EP | 1 312 304 | 5/2003 |

(Continued)

OTHER PUBLICATIONS

Hoshiyama et al. "Peripheral nerve conduction recorded by a micro gradiometer system (micro-SQUID) in humans." *Neuroscience Letters* 272.3 (1999): 199-202.

(Continued)

*Primary Examiner* — Rochelle D Turchen
(74) *Attorney, Agent, or Firm* — Dunlap Codding, P.C.

(57) ABSTRACT

A neurophysiological monitoring system includes at least one surgical instrument having at least one magnetometer and a control unit configured to receive magnetic field data generated by the at least one magnetometer. The control unit may provide stimulation to a nerve at a known stimulation time and receive magnetic field data from the at least one magnetometer indicative of a response to stimulation of the nerve at a receive time. An interpretation of the magnetic field data based upon the receive time and the stimulation time may be generated.

17 Claims, 9 Drawing Sheets

(56) References Cited

U.S. PATENT DOCUMENTS

| | | | | |
|---|---|---|---|---|
| 2014/0243750 | A1* | 8/2014 | Larsen | A61M 5/1452 604/189 |
| 2015/0032022 | A1 | 1/2015 | Stone et al. | |
| 2016/0101289 | A1* | 4/2016 | Stolen | A61N 1/36135 600/516 |

FOREIGN PATENT DOCUMENTS

| | | |
|---|---|---|
| FI | 924328 | 3/1994 |
| JP | 06-285032 | 10/1994 |
| JP | 11-104094 | 4/1999 |
| JP | 11-104099 | 4/1999 |
| JP | 11-151220 | 6/1999 |
| JP | 2000-262483 | 9/2000 |
| JP | 2000-287947 | 10/2000 |
| JP | 2000-300530 | 10/2000 |
| JP | 2001-078975 | 3/2001 |
| JP | 2001-104262 | 4/2001 |
| JP | 2001-104267 | 4/2001 |
| JP | 2004-041789 | 2/2004 |
| JP | 2004-089724 | 3/2004 |
| JP | 2004-209302 | 7/2004 |
| JP | 2004-216184 | 8/2004 |
| JP | 2004-358278 | 12/2004 |
| JP | 2004-358279 | 12/2004 |
| JP | 2005-028164 | 2/2005 |
| JP | 2006-304851 | 11/2006 |
| JP | 2007-181564 | 7/2007 |
| JP | 2007-181566 | 7/2007 |
| JP | 2007-203098 | 8/2007 |
| JP | 2008-178558 | 8/2008 |
| JP | 2008-206809 | 9/2008 |
| JP | 2009-034404 | 2/2009 |
| JP | 2010-035595 | 2/2010 |
| JP | 2010-035596 | 2/2010 |
| WO | 2002/097461 | 12/2002 |
| WO | 2011/057274 | 5/2011 |

OTHER PUBLICATIONS

International Search Report and Written Opinion (PCT/IB2016/001008); dated Jan. 18, 2017.

Silverstein et al. "Saphenous Nerve SSEP: A Novel Technique for the Reduction of Femoral Nerve Injury during Transpsoas Lateral Access Surgery." Retrieved from the Internet: http://unpa.pro/Saphenous_Nerve_SSEP_for_Lateral_Access_Lumbar_Surgery, May 15, 2014.

"SpinTJ Magnetic Field Sensors." Micro Magnetic, Inc. Retrieved from the Internet: http://micromagnetics.com/products_mtj_f_s.html, Jun. 29, 2015.

Wikswo et al. "Magnetic Field of a Nerve Impulse: First Measurements." *Science* 208.4439 (1980): 53-55.

Chinese Search Report (Chinese application No. 201680036698.X); dated Jan. 6, 2020; Depuy Synthes Products, Inc.; 2 pages.

Australian Examination Report No. 1 dated Dec. 18, 2019 (Australian application No. 2016281812); 4 pages.

\* cited by examiner

INTRAOPERATIVE MAGNETOMETRY MONITORING SYSTEM

CROSS-REFERENCE TO RELATED APPLICATIONS

Not applicable.

BACKGROUND

Intraoperative physiological monitoring is a continually evolving field that aims to localize, monitor and preserve the structural and/or functional integrity of structures during surgery or other invasive procedures. For example, during spinal surgery, several neural structures may be placed at risk for potential injury (e.g., spinal cord, one or more nerve roots, lumbar plexus, vascular supply members). Generally, intraoperative physiological monitoring seeks to preserve the structural and/or functional integrity of the neural structures during surgery or other invasive procedures.

Several modalities are currently available for monitoring various aspects of the central and peripheral nervous system during surgery or other invasive procedures in order to maintain structural and/or functional integrity. Each neural monitoring modality offers a unique set of benefits and limitations as well as offering varying degrees of sensitivity or specificity. For example, the most frequently used neural monitoring modalities for spinal procedures include somatosensory evoked potentials (SSEPs), motor evoked potentials (MEPs), freerun or spontaneous EMG (sEMG), and triggered EMG (tEMG).

In lateral spine surgery, for example, the psoas muscle may be traversed by access instruments and retractors. Currently, a triggered EMG technique is used within the industry to estimate the distance of probes and instruments from nerves near the access path. Triggered EMG, however, requires a specialized suboptimal anesthesia protocol that does not paralyze the patient during the procedure. Additionally, triggered EMG does not test sensory nerves within the region of interest. Further, triggered EMG does not give information on relative health of the nerve during the procedure. As such, other modalities of intraoperative physiological monitoring are needed.

BRIEF DESCRIPTION OF THE SEVERAL VIEWS OF THE DRAWINGS

Like reference numerals in the figures represent and refer to the same or similar element or function. Implementations of the disclosure may be better understood when consideration is given to the following detailed description thereof. Such description makes reference to the annexed pictorial illustrations, schematics, graphs, drawings, and appendices.

DETAILED DESCRIPTION OF INVENTIVE CONCEPT(S)

Figure 1:
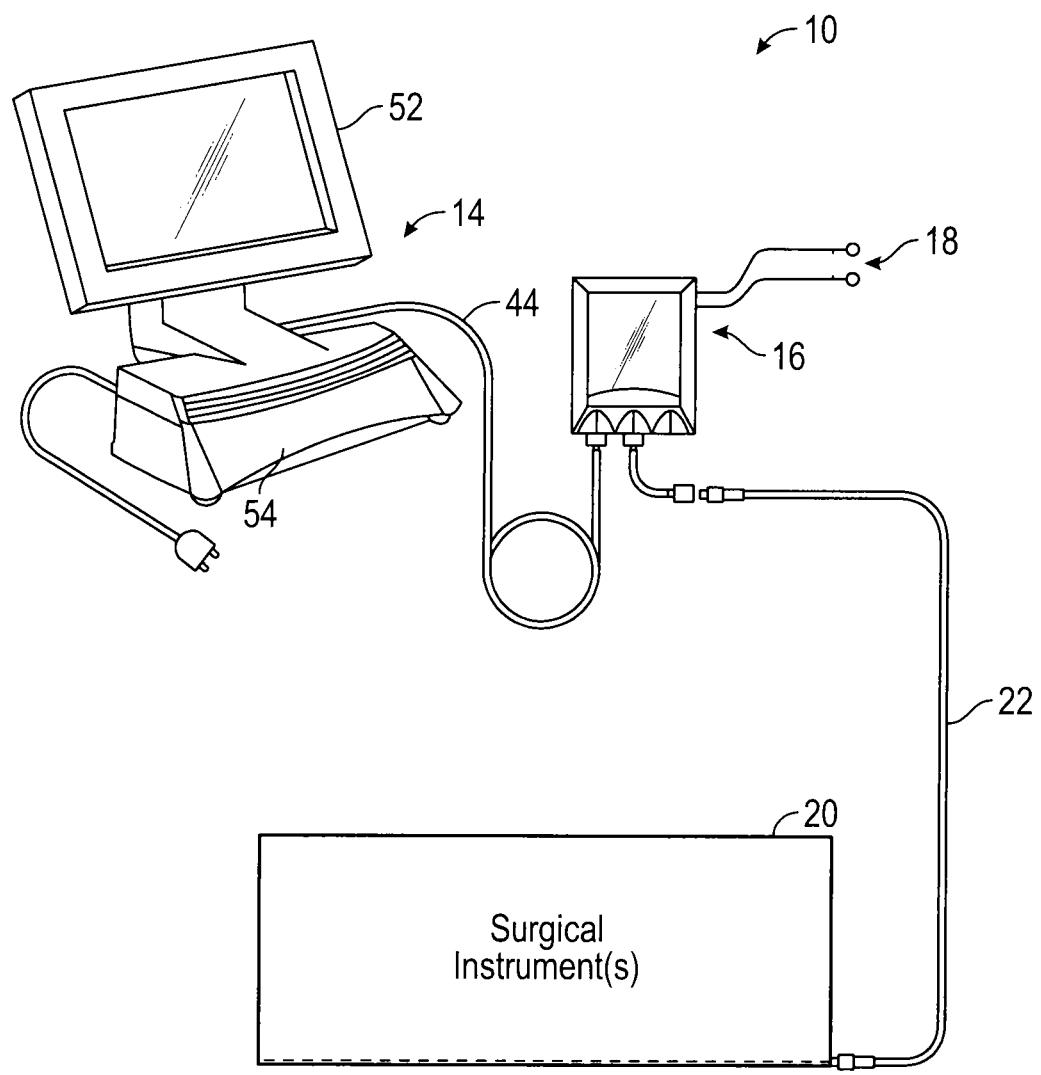
FIG. 1 is a diagrammatic view of an exemplary intraoperative magnetometry monitoring system in accordance with the present disclosure.

Before explaining at least one embodiment of the inventive concept(s) disclosed herein in detail, it is to be understood that the presently disclosed and claimed inventive concept(s), process(es), methodology(ies), and/or outcome(s) is not limited in its application to the details of construction and the arrangement of the components or steps or methodologies set forth in the following description or illustrated in the drawings. The presently disclosed and claimed inventive concept(s), process(es), methodology(ies), and/or outcome(s) disclosed herein may be capable of other embodiments or of being practiced or carried out in various ways. Also, it is to be understood that the phraseology and terminology employed herein is for the purpose of description and should not be regarded as limiting the presently disclosed and claimed inventive concept(s), process(es), methodology(ies), and/or outcome(s) herein in any way. With respect to any reference—patent or otherwise—mentioned herein, such reference should be considered to be incorporated by reference herein in its entirety as if set forth explicitly herein.

In the following detailed description of embodiments of the presently disclosed and claimed inventive concept(s), process(es), methodology(ies), and/or outcome(s), numerous specific details are set forth in order to provide a more thorough understanding of the presently disclosed and claimed inventive concept(s), process(es), methodology(ies), and/or outcome(s). However, it will be apparent to one of ordinary skill in the art that the presently disclosed and claimed inventive concept(s), process(es), methodology(ies), and/or outcome(s) within the disclosure may be practiced without one or more of these specific details, by skipping one or more of these specific details, or by modifying or transforming one or more of these specific details in a manner that would be apparent to one or ordinary skill in the art given the present disclosure and teachings. In other instances, well-known features have not been described in detail to avoid unnecessarily complicating the instant disclosure and teachings and the following specification should be construed as including all relevant and/or known details or teachings that would be within the skill and knowledge of one of ordinary skill in the art.

The presently disclosed and claimed inventive concept(s), process(es), methodology(ies), and/or outcome(s) disclosed herein are generally directed to an intraoperative magnetometry monitoring system for use in spinal surgery, for example. The intraoperative magnetometry monitoring system may permit a surgeon to be capable of monitoring nerve health and/or orientation of the nerve relative to a surgical instrument. The presently disclosed and taught intraoperative magnetometry system may provide a surgeon with information regarding the status of various nerves or other neural structures within the patient, as well as other information useful in obtaining a successful surgical outcome. The intraoperative magnetometry system will be described hereinafter in the context of spinal surgery, however, it is to be understood and would be understood by one of ordinary skill in the art given the present disclosure and teachings, that the presently disclosed and claimed inventive concept(s), process(es), methodology(ies), and/or outcome(s) are equally applicable to other types of surgical procedures wherein magnetometry may be used to provide feedback to surgeons and/or surgical tools.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements, but may include other elements not expressly listed.

As used herein the notation "a-n" appended to a reference numeral is intended as merely convenient shorthand to reference one, or more than one, and up to infinity, of the elements or features identified by the respective reference numeral (e.g., 134a-n). Similarly, a letter following a reference numeral is intended to reference an embodiment of the features of an element that may be similar, but not necessarily identical, to a previously described element or feature bearing the same reference numeral (e.g., 148, 148a, 148b, etc.). Such shorthand notations are used for purposes of clarity and convenience only, and should not be construed to limit the presently disclosed and claimed inventive concept(s), process(es), methodology(ies), and/or outcome(s) in any way, unless expressly stated to the contrary.

Further, unless expressly stated to the contrary, "or" refers to an inclusive "or" and not to an exclusive "or." For example, a condition A or B is satisfied by anyone of the following: A is true (or present) and B is false (or not present), A is false (or not present) and B is true (or present), and both A and B are true (or present).

In addition, use of the term "a" or "an" are employed herein to describe elements and components of the embodiments herein. This is done merely for convenience and to give a general sense of the presently disclosed and claimed inventive concept(s), process(es), methodology(ies), and/or outcome(s). This description should be read to include one or at least one and the singular also includes the plural unless it is readily apparent to one or ordinary skill in the art that it is meant otherwise.

Finally, as used herein, any reference to "one embodiment," "some embodiments," or "an embodiment" means that a particular element, feature, structure, or characteristic described in connection with the embodiments is included in at least one embodiment of the presently disclosed and claimed inventive concept(s), process(es), methodology(ies), and/or outcome(s). The appearance of the phrases "in one embodiment," "in some embodiments," and "in an embodiment" in various places in the specification do not necessarily refer to the same embodiment unless it would be readily apparent to one of ordinary skill in the art that it is meant otherwise.

Figure 2:
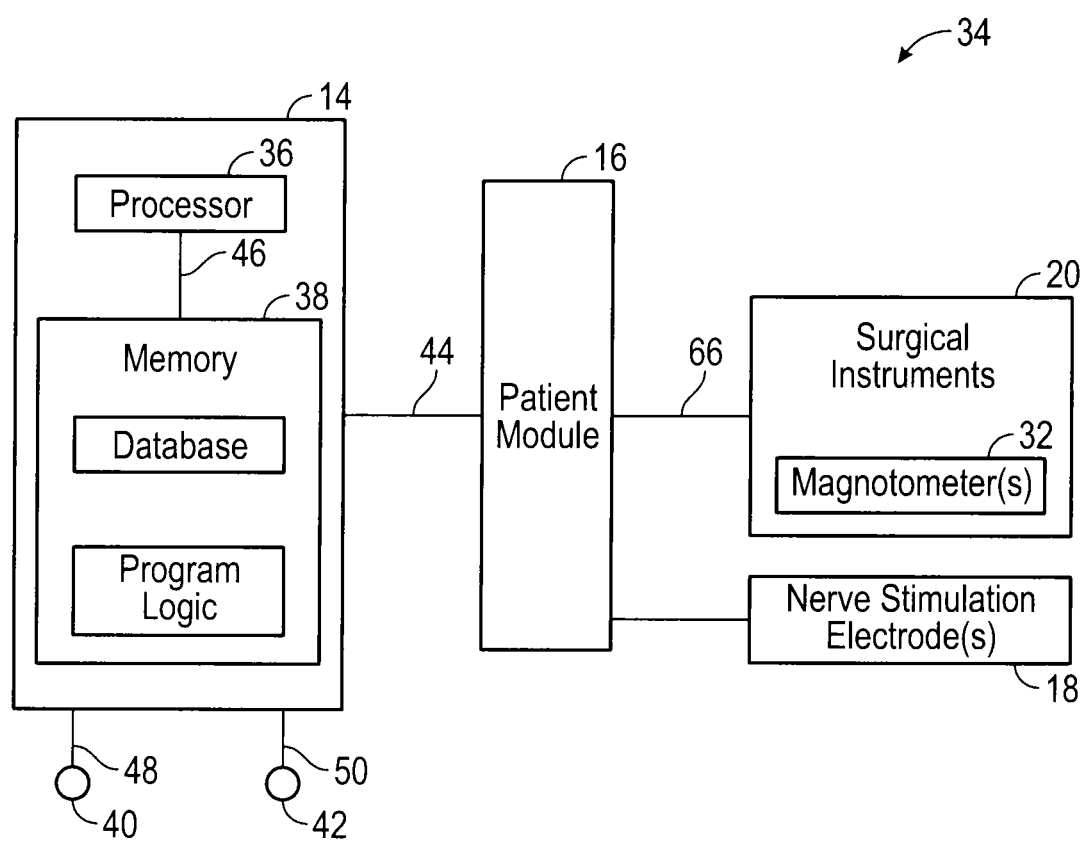
FIG. 2 is another diagrammatic view of the intraoperative magnetometry monitoring system illustrated in FIG. 1.

Referring now to the Figures, and in particular to FIGS. 1 and 2, illustrated therein is an exemplary embodiment of an intraoperative magnetometry monitoring system 10 (hereinafter referred to as "monitoring system 10") capable of and configured to employ nerve proximity, nerve direction, and/or nerve pathology assessments according to the presently disclosed and claimed inventive concept(s), process(es), methodology(ies), and/or outcome(s). It is expressly noted that, although described herein largely in terms of use in spinal surgery, the monitoring system 10 and related methods of the presently disclosed and claimed inventive concept(s), process(es), methodology(ies), and/or outcome(s) may be suitable for use in any number of additional surgical procedures wherein tissue having neural structures may present.

The monitoring system 10 includes a control unit 14, a patient module 16, one or more nerve stimulation electrode 18 (referred to hereinafter as "nerve stimulation electrode 18" or "nerve stimulation electrodes 18", as appropriate) and one or more surgical instrument 20 (referred to hereinafter as "surgical instrument 20" or "surgical instruments 20", as appropriate) capable of being coupled to the patient module 16 via one or more accessory cable 22, as appropriate. The surgical instrument 20 may include, but is not necessarily limited to, surgical access components (e.g., probe, dilator(s), working dilator(s), retractors), and/or one or more neural pathology monitoring devices (e.g., nerve root retractor). As shown in FIG. 1, the surgical instrument 20 is coupled to the patient module 16 via the one or more accessory cable 22. It should also be understood that a wireless link (using any suitable communication technology such as the technology known as "Bluetooth" can be used to couple the one or more surgical instrument 20 with the patient module 16.

One or more magnetometer 32 (referred to hereinafter as "magnetometer 32" or "magnetometers 32", as appropriate) may be positioned on the surgical instrument 20. Magnetic field signals generated by one or more nerves may be detected using the one or more magnetometer 32. For example, one or more nerves may be stimulated by application of an electrical current by the nerve stimulation electrodes 18 on a first side of an access site such that the one or more nerves generate a magnetic field. As an action potential of the nerve moves along the nerve's path, at a second site, at least one of an orientation and magnitude of the magnetic field may be measured by the one or more magnetometer 32. Time between stimulation and measurement may be related to the nerve conduction velocity (NCV) as described in further detail herein. As such, the speed at which the signal traverses may be related to health of the one or more nerves such speed may be measured by the monitoring system 10 based upon signals generated by the one or more magnetometer 32.

FIG. 2 illustrates a block diagram 34 of the monitoring system 10 illustrated in FIG. 1. Generally, the control unit 14 comprises one or more processors 36 capable of executing processor executable code, one or more non-transitory memory 38 (referred to herein as "memory 38") capable of storing processor executable code, an input device 40, and an output device 42. The control unit 14 may communicate with the patient module 16 via path 44, which may be any suitable communication links such as a cable, a bus, or a wireless link. The processor executable code causes the processor 36 to activate at least one nerve stimulation electrode 18 providing stimulation to a nerve; receive magnetic field data from the one or more magnetometer 32 indicative of a response to stimulation of the nerve; interpret the magnetic field data; and, output information indicative of the interpretation. Any suitable technique can be used to interpret the magnetic field data. For example, the processor executable code can be configured to utilize techniques known in the art such as the electrical technique and the magnetic technique. The electrical technique and the magnetic technique are discussed within an article identified by Wijesinghe RS (2014) Detection of Magnetic Fields Created by Biological Tissues. J Electr Electron Syst 3: 120, which article is hereby incorporated herein by reference.

The processor 36 may be implemented as a single processor or multiple processors working together to execute the logic described herein. Each processor 36 may be capable of reading and/or executing code and/or capable of creating, manipulating, retrieving, altering and/or storing data structure. Exemplary embodiments of the one or more processors 36 include, but are not limited to, digital signal processors (DSPs), central processing units (CPUs), field programmable gate arrays (FPGAs), microprocessors, multi-core processors, combinations thereof, and/or the like.

The processor 36 may be capable of communicating with the one or more memory 38 via a path 46 which may be implemented as a data bus, for example. The program logic can cause the processor 36 to record a baseline NCV for the nerve being studied and use a percent reduction from the baseline NCV as a trigger to alert the surgeon to potential degradation of nerve health. The relative amplitude of the magnetic response of the nerve is directly related to the distance between the nerve and the magnetometer 32. With two or more magnetometers 32 and samples of Action Potentials recorded at multiple locations as the surgical instrument 20 is advanced, triangulation techniques based off peak potentials may be used to locate the nerve's position. The techniques may account for the three dimensional character of the action potential traveling along the nerve. It is important to note that there is an essentially zero conduction delay in the magnetic signal from the nerve to the magnetometer(s) 32 and so time locked recordings and relative amplitudes can be used to triangulate. The amplitude of the magnetic response will change with respect to the orientation of the nerve and the nnagnetometer(s) 32. Exploiting that effect may provide another technique to judge when the magnetometer(s) 32 has moved past the nerve. Orientation and mapping of the nerve in space can be established uniquely with the 3D location of the magnetometer(s) 32 and the signals recorded at multiple locations. The processor 36 may be capable of communicating with the input device 40 and the output device 42 via paths 48 and 50, respectively. Paths 48 and 50 may be implemented similarly to, or differently from, path 46.

In some embodiments, interfacing or connecting over paths 44, 46, 48 and/or 50 may include one or more networks. Paths 44, 46, 48 and/or 50 may use one or more network topographies and/or protocols, including, but not limited to, Bluetooth, Wi-Fi, biotelemetry, infrared (IR), ultrasound, Ethernet, TCP/IP, circuit switched paths, combinations thereof, and/or the like. For example, one or more physical or virtual ports may use a network protocol such as TCP/IP, for example, to exchange electronic, digital, and/or optical signals. In some embodiments, the one or more networks may be implemented as the World Wide Web (or internet), a local area network (LAN), a wide area network (WAN), a wireless local area network (WLAN), a metropolitan network, a wireless network, a cellular network, a GSM-network, a CDMA network, a 3G network, a 4G network, a satellite network, a radio network, an optical network, a cable network, a public switch telephone network, an Ethernet network, combinations thereof, and/or the like. Additionally, the paths 44, 46, 48 and/or 50 may use a variety of protocols to permit uni-directional or bi-directionally interface and/or communication of data and/or information.

In some embodiments, the processor 36 may include two or more processors located remotely from one another and use a network protocol to communicate therebetween. To that end, in some embodiments, each element of the control unit 14 may be partially or completely net-worked based or cloud-based, and may not be located in a single physical location. The network may permit uni-directional or bi-directional communication of information and/or data between the processor 36, the one or more memory 38, the one or more input devices 40 and/or the one or more output device 42. As used herein, the terms "network-based," "cloud-based," and any variation thereof, are intended to include the provision of configurable computational resources on demand via interfacing with a computer and/or a computer network, with software and/or data at least partially located on the computer and/or computer network.

The processor 36 may be capable of communicating with the one or more memory 38 via the path 46. The one or more memory 38 may be capable of storing processor executable code. Additionally, the one or more memory 38 may be implemented as a conventional non-transitory memory, such as, for example, random access memory (RAM), a CD-ROM, a hard drive, a solid state drive, a flash drive, a memory card, a DVD-ROM, a floppy disk, an optical drive, combinations thereof, and/or the like.

The one or more memory 38 may be located in the same physical location as the processor 36, or located remotely from the processor 36 and may communicate with the processor 36 via a network as described herein. Additionally, when more than one memory 38 is used, one or more memory 38 may be located in the same physical location as the processor 36, and one or more memory 38 may be located in a remote physical location from the processor 36. The physical location(s) of the one or more memory 38 may be varied. In some embodiments, the one or more memory 38 may be implemented as a "cloud memory" (i.e., one or more memory may be partially, or completely base don or accessed using the network as described herein).

The input device 40 may transmit data to the processor 36 and may be implemented as a keyboard, a mouse, a touchscreen, a camera, a cellular phone, a tablet, a smart phone, a personal digital assistant (PDA), a microphone, a network adapter, a probe having a sensor therein, a microcapillary testing device or array, a microfluidic testing device, combinations thereof, for example but not by way of limitation. Any device capable of functionally transmitting data to the processor 36 may be used as the input device 40. The input device 40 may be located in the same physical location as the processor 36, or may be remotely located and/or partially or completely network-based. The input device 40 communicates with the processor 36 via the path 48.

The output device 42 may transmit information from the processor 36 to a user, such that the information may be perceived by the user. For example, but not by way of limitation, the output device 42 may be implemented as a server, a computer monitor, a cell phone, a tablet, a speaker, a website, a PDA, a fax, a printer, a projector, a laptop monitor, combinations thereof, and/or the like. The output device 42 may be physically co-located with the processor 36, or may be located remotely from the processor 36, and may be partially or completely network-based (e.g., a website). The output device 42 may communicate with the processor 36 via the path 50. As used herein, the term "user" is not limited to a human, and may comprise a human using a computer, a host system, a smart phone, a tablet, a computerized pen or writing device, combinations thereof, and/or the like, for example, but not by way of limitation.

In some embodiments, the control unit 14 may include a touch screen display 52 and a base 54 as illustrated in FIG. 1. The touch screen display 52 may form the input device 40 and the output device 42. The touch screen display 52 may be equipped with a graphical user interface (GUI) capable of communicating information to the user and receiving instructions from the user. The base 54 may form a housing containing the hardware and/or software implementing the processor 36 and/or the memory 38 to control the nerve stimulation electrodes 18, receive digitized signals and other information from the patient module 16, processes neural monitoring, and/or display processed data to a user. For example, software stored on the one or more memory 38 of the control unit 14 may receive one or more commands (e.g., via the touch screen display 52 to provide activation of stimulation in a requested mode of available surgery modes, processing signal data according to defined algorithms stored on the one or more memory 38, displaying received parameters and/or processed data, and/or monitoring system status and reporting fault conditions, for example.

In some embodiments, the control unit 14 may be situated outside but close to the surgical field (e.g., on a cart adjacent to an operating table). For example, the control unit 14 may be situated on a cart adjacent to an operating table with the touch screen display 52 directed towards the surgeon for easy visualization. In some embodiments, one or more components of the control unit 14 may be situated outside of the operating environment with one or more components of the control unit 14 situated outside but close to the surgical field. For example, the output device 42 (e.g., speaker headset) may provide direction and instruction to the surgeon with the remaining components of the control unit 14 communicating via a network and positioned outside of the operating environment.

The patient module 16 may communicate with the control unit 14 via the path 44. In some embodiments, the patient module 16 may be located between a patient's legs, or may be affixed to an end of the operating table at mid-leg level using a clamp, for example. The position may be selected such that leads may reach a desired location without tension during a surgical procedure. It should be noted, in some embodiments, the control unit 14 may communicate directly with the nerve stimulation electrode(s) 18 and/or the surgical instrument(s) 20 without the use of the patient module 16.

Figure 3A:
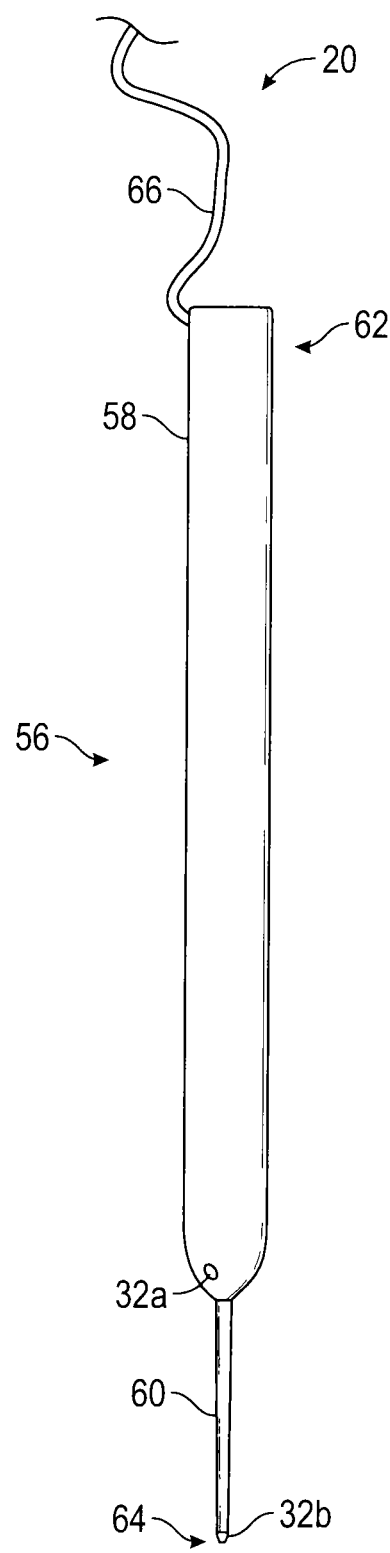
FIG. 3A is a side view of an exemplary neuromonitoring dilator for use in the intraoperative magnetometry monitoring system illustrated in FIG. 1.
Figure 3B:
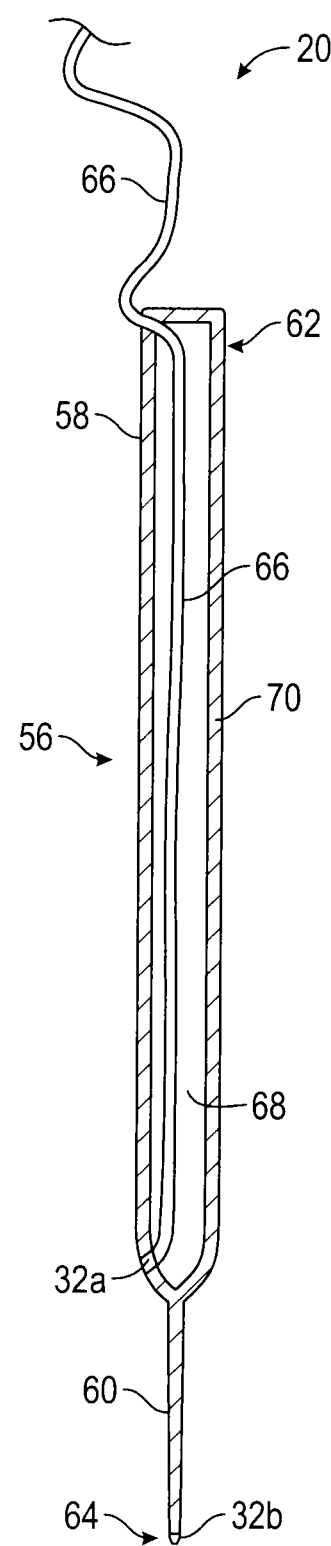
FIG. 3B is a cross sectional view of the neuromonitoring dilator illustrated in FIG. 3A.
Figure 4:
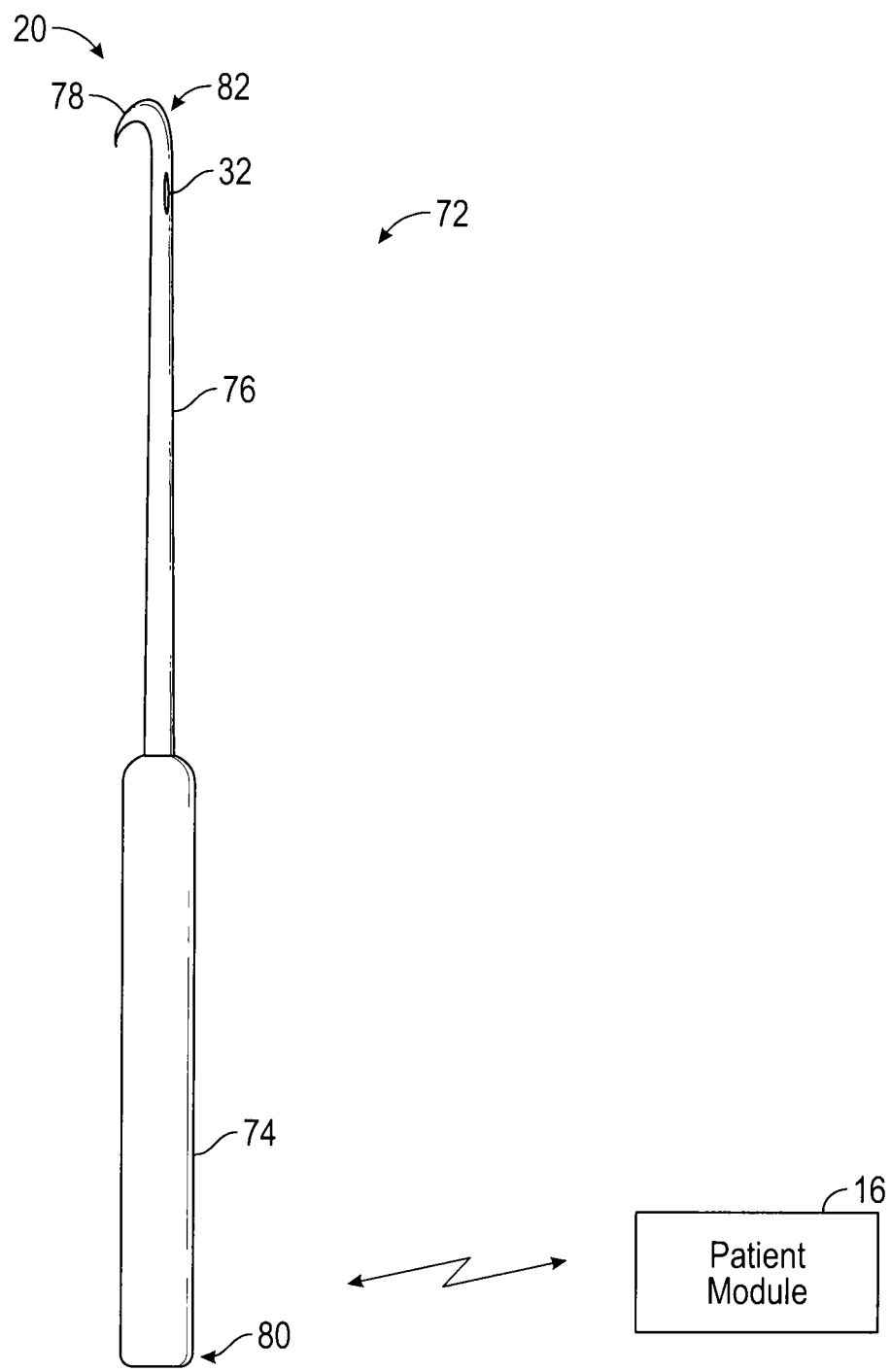
FIG. 4 is a side view of an exemplary neuromonitoring nerve root retractor for use in the intraoperative magnetometry monitoring system illustrated in FIG. 1.

FIGS. 3-4 illustrate exemplary surgical instruments 20 for use in the monitoring system 10. Generally, each surgical instrument 20 includes one or more magnetometer 32. Each magnetometer 32 is configured in a specific detection orientation to measure magnetic fields generated by electrically active nerves that create propagating action potentials and magnetic fields.

In some embodiments, the one or more magnetometer 32 may include a fluxgate circuit, superconducting quantum interference device (SQUID), spin exchange relaxation-free (SERF), magnetoresistive, Hall effect, rotating coil, vector, caesium vapour, and/or the like. In some embodiments, scalar magnetometer technologies may also be used including, but not limited to overhauser and proton precession. In some embodiments, laboratory magnetometer technologies may be applied including, but not limited to inductive pickup coils, vibrating sample, pulsed field extraction, torque, faraday force, optical, and/or the like. Additionally, in some embodiments, MEMS Loretz-force based, MEMS voltage sensing, MEMS frequency shift sensing, and/or MEMS Optical based sensing technologies may be used, for example.

In some embodiments, a plurality of magnetometers 32 may be spatially distributed on one or more surgical instruments 20 and/or within the surgical environment. Use of spatially distributed multiple magnetometers 32 may provide for derivation of three-dimensional positional information of a stimulated nerve. The spatially distributed magnetometers 32 may be fixed at known locations and/or orientations relative to one another to assist in correlating data generated by the spatially distributed magnetometers 32. For example, in some embodiments, each of the magnetometers 32 may measure along an orthogonal axis. For example, one of the magnetometers 32 (which may be referred to herein as a "first magnetometer") may be positioned such that a measurement axis aligns along an X-axis of the surgical instrument 20. Another one of the magnetometers 32 (which may be referred to herein as a "second magnetometer") may be positioned such that a measurement axis aligns along a Y-axis of the surgical instrument 20. Yet another one of the magnetometers 32 (which may be referred to herein as a "third magnetometer") may be positioned such that a measurement axis aligns along a Z-axis of the surgical instrument 20. It should be noted that the one or more magnetometers 32 may be intentionally offset from the axes of the surgical instrument 20. As one skilled in the art will appreciate, transformations may be performed on data collected from the magnetometers 32. For simplicity, such systems are not explicitly described herein, however, one skilled in the art will appreciate, the present disclosure may be applied to such systems.

In some embodiments, signal amplitude collected by the magnetometers 32 may be analyzed and correlated to a distance from the stimulated nerve to one or more of the magnetometers 32. Repositioning of one or more magnetometers 32 and examination of further stimulation responses may provide directional information with regard to the position and orientation of a longitudinal axis of the stimulated nerve.

FIGS. 3A and 3B illustrate an exemplary embodiment of an exemplary surgical instrument 20 for use within the monitoring system 10 of FIG. 1. In particular, FIGS. 3A and 3B illustrate a neuromonitoring dilator 56 constructed in accordance with the concepts disclosed herein. The neuromonitoring dilator 56 may generate data indicative of magnetic fields being generated by one or more nerve so as to assist in monitoring the magnetic fields for determination of the presence and/or proximity of nerves during introduction of the neuromonitoring dilator 56 into the spine and/or other body part(s), while simultaneously creating and/or enlarging one or more surgical corridors.

The neuromonitoring dilator 56 may include a dilator portion 58 and a probe portion 60. The dilator portion 58 and the probe portion 60 may be positioned at opposing ends such that the dilator portion 58 is positioned at a proximal end 62 and the probe portion 60 at a distal end 64 of the neuromonitoring dilator 56. As shown in FIGS. 3A and 3B, the dilator portion 58 may be of tubular construction and may be tapered adjacent to an intersection of the dilator portion 58 and the probe portion 60. The dilator portion 58 and the probe portion 60 may be made of a non-magnetically conductive material such as austenitic stainless steel, aluminum, biocompatible plastic or the like such that the dilator portion 58 and the probe portion 60 do not interfere with the receipt of electromagnetic signals by the one or more magnetometers 32.

The dilator portion 58 and/or the probe portion 60 may support and be coupled to, e.g., house, at least one or more magnetometer 32. For example, in FIG. 3A, the dilator portion 58 includes a magnetometer 32a and the probe portion 60 includes a magnetometer 32b. In some embodiments, the one or more magnetometer 32 may be partially embedded within the neuromonitoring dilator 56 such that a portion of the magnetometer(s) 32 may be exposed, may be connected via adhesive, or provided in any other suitable fashion, for example.

A communication link 66 may connect the one or more magnetometer 32 of the neuromonitoring dilator 56 to the patient module 16. In some embodiments, the communication link 66 may include a wired connection capable of communicating data between the one or more magnetometer 32 of the neuromonitoring dilator 56 and the patient module 16 as illustrated in FIGS. 1, 3A and 3B. To that end, the communication link 66 may connect the one or more magnetometer 32 to the patient module 16, or communication link 66 may connect circuitry associated with the one or more magnetometer 32 to the patient module 16. The neuromonitoring dilator 56 may be provided with circuitry for collecting and conditioning signals generated by the one or more magnetometer 32. In one embodiment, the signals may be analog electrical signals and the circuitry may include, but is not limited to, an amplifier, an analog-to-digital converter, a transceiver or the like for transforming the analog electrical signals into a format that can be transmitted to the patient module 16 via the communication link 66. The communication link 66 may be positioned within the lumen 68 of the dilator portion 58. Alternatively, the communication link 66 may be positioned on and/or inside an exterior surface 70 of the dilator portion 58 (e.g., via one or more channels).

One or more additional magnetometer 32 may be positioned about the dilator portion 58 and/or the probe portion 60 and communicate data to the patient module 16 via the communication link 66. For example, additional magnetometers 32 may be positioned on the proximal end 62 of the dilator portion 58 and communicate data to the patient module 16 via the communication link 66. In some embodiments, the communication link 66 may include a wireless connection such that data generated by the magnetometer 32a and the magnetometer 32b may be communicated between the magnetometers 32a and 32b and the patient module 16 via a wireless network, for example.

FIG. 4 illustrates another exemplary embodiment of an exemplary surgical instrument 20 for use within the monitoring system 10 of FIG. 1. In particular, FIG. 4 illustrates a neuromonitoring nerve root retractor 72. The neuromonitoring nerve root retractor 72 may monitor magnetic fields for determination of the presence and/or proximity of nerves during introduction into the spine and/or other body part(s), while simultaneously altering position of a nerve root.

The neuromonitoring nerve root retractor 72 may include a handle 74, a shaft 76, and a hook 78. The handle 74 may be positioned on the proximal end 80 of the neuromonitoring nerve root retractor 72 and the hook 78 may be positioned on the distal end 82 of the neuromonitoring nerve root retractor 72 with the shaft 76 extending between the handle 74 and the hook 78. In some embodiments, the shaft 76 may be a linear shaft as illustrated in FIG. 4. However, it should be apparent to one skilled in the art, the shaft 76 may be linear and/or adjustable such that during use the shaft 76 may be angled.

In some embodiments, one or more magnetometer 32 may be positioned on the handle 74, the shaft 76, and/or the hook 78. For example, in FIG. 4, the magnetometer 32 is positioned on the shaft 76 of the neuromonitoring nerve root retractor 72 adjacent to the hook 78 so as to be in close proximity to the nerves and/or tissues that the hook 78 is being used to move.

The communication link 66 may connect the neuromonitoring nerve root retractor 72 to the patient module 16. In some embodiments, the communication link 66 may be wireless and capable of communicating data being generated by the one or more magnetometer 32 to the patient module 16 as illustrated in FIG. 4. In this example, the communication link 66 may be positioned on the exterior of the neuromonitoring nerve root retractor 72. In some embodiments, the communication link 66 may include transmission of data over a network as further described herein.

Alternatively, in some embodiments, the communication link 66 may be wired. For example, the communication link 66 may be a wired connection connecting the magnetometer 32 with the patient module 16. The wired connection may be positioned on an interior of the neuromonitoring nerve root retractor 72 (e.g., within a lumen), for example.

One or more additional magnetometer 32 may be positioned about the handle 74, the shaft 76 and/or the hook 78. For example, multiple magnetometers 32 may be positioned on the handle 74.

In some embodiments, one or more magnetometer 32 may be positioned on a retractor having one or more blades. For example, the one or more magnetometer 32 may be partially embedded in or placed on one or more blades as previously described.

Figure 9:
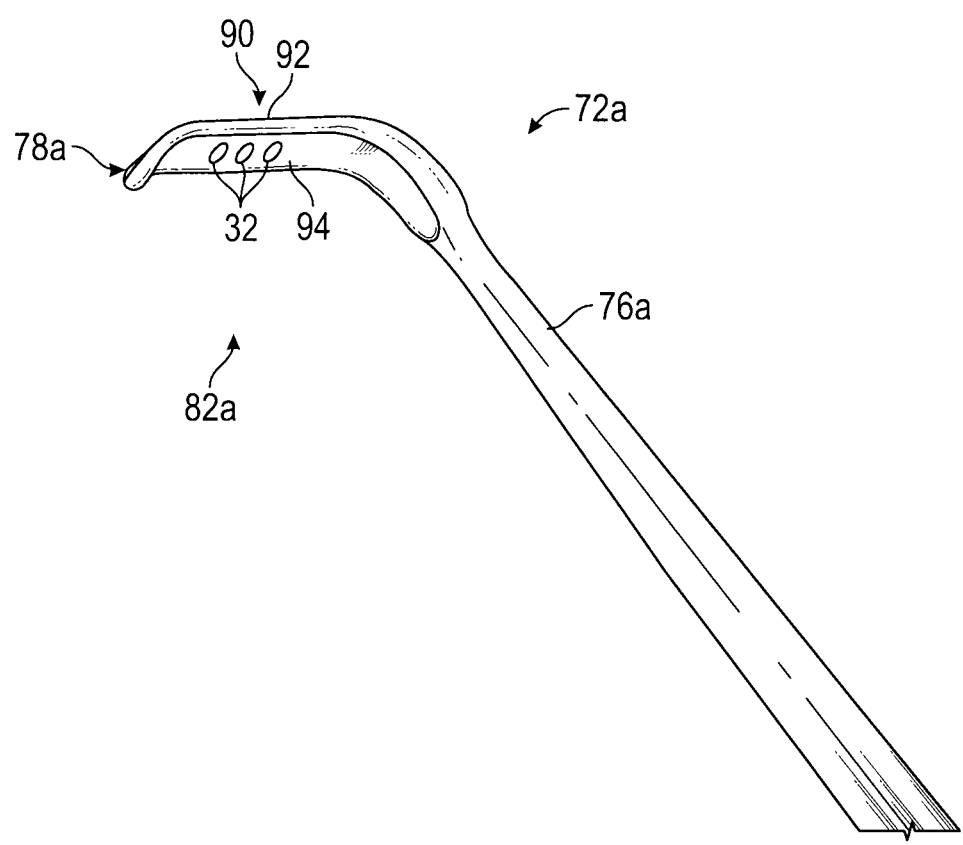
FIG. 9 is another exemplary embodiment of a distal end of a neuromonitoring nerve root retractor for use in the intraoperative magnetometry monitoring system illustrated in FIG. 1.

FIG. 9 illustrates a distal end 82a of another exemplary neuromonitoring nerve root retractor 72a. The neuromonitoring nerve root retractor 72a may monitor magnetic fields for determination of the presence and/or proximity of nerves during introduction of the nerve root retractor 72a into the spine and/or other body part(s), while simultaneously altering position of a nerve root.

The distal end 82a of the neuromonitoring nerve root retractor 72a may include a hook 78a connected to a shaft 76a. The distal end 82a may also include a mounting portion 90 extending between the hook 78a and the shaft 76a. In some embodiments, the mounting portion 90 may be a flat panel having a first side 92 and a second side 94 (e.g., opposite the first side 92) as illustrated in FIG. 9. One or more magnetometers 32 may be positioned on the first side 92 and/or the second side 94 of the mounting portion 90. For example, in some embodiments, multiple magnetometers 32 may be positioned on the second side 94 of the mounting portion 90. Although the mounting portion 90 is illustrated as a flat panel, it should be noted that the mounting portion 90 may include one or more recesses, panels, and/or the like aiding in positioning of one or more magnetometers 32 on the mounting portion 90.

Figure 5:
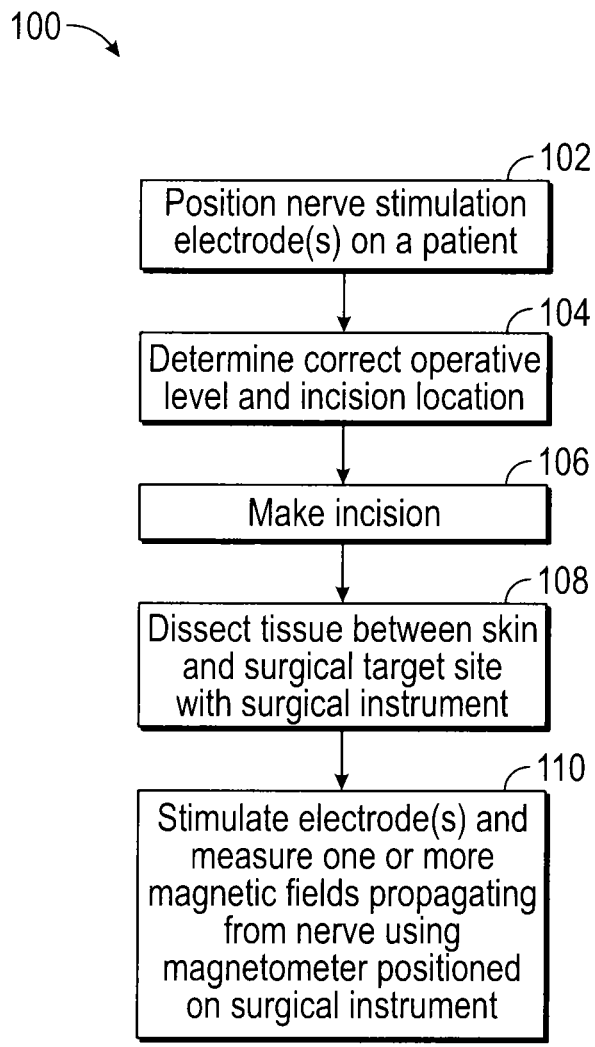
FIG. 5 is a flow chart of an exemplary method of using the intraoperative magnetometry monitoring system illustrated in FIG. 1.

FIG. 5 illustrates a flow chart 100 of an exemplary method of using the system 10 as disclosed herein. Generally, the monitoring system 10 stimulates nerves via the one or more nerve stimulation electrode 18 while monitoring a magnetic field response transmitted by the nerve. In a step 102, at least one nerve stimulation electrode 18 may be positioned on a patient for stimulation of one or more predetermined nerve(s). The nerve stimulation electrode 18 may be surface electrodes, needle electrodes, a combination of both, and/or the like. For example, in some embodiments, electrical stimulation provided by the nerve stimulation electrode 18 may be applied at the periphery of a nerve such that conduction is transmitted towards the nerve root (e.g., application at the saphenous nerve 84 illustrated in FIG. 6 at the anterior medial thigh between the Sartorius and Vastus medialis muscles). As one skilled in the art will appreciate, additional nerve stimulation electrodes 18 may be applied downstream in order to ensure the exiting nerve root is ennervated. For example, additional nerve stimulation may be applied to the anterior cutaneous nerve 86 as well.

In some embodiments, in the step 102, the control unit 14 may verify that one or more nerve stimulation electrode 18 is positioned correctly and functioning correctly. If positioned incorrectly, the control unit 14 may provide a signal (e.g., visual, auditory, tactile,) via the output device 42 indicating repositioning may be needed. If positioned correctly, the control unit 14 may also provide a signal (e.g., visual, auditory, tactile,) via the output device 42 indicating correct positioning for a particular procedure.

In a step 104, a correct operative level and incision may be determined. For example, in some embodiments, the correct operative level and incision may be determined using fluoroscopy views as known in the art. In a step 106, an incision may be made in the patient. With an incision made, the subcutaneous tissue may be taken down with oblique muscles of the abdomen visible.

In a step 108, one or more surgical instrument 20 may be used to dissect tissue between the patient's skin and a surgical target site 120 through the oblique muscles, the retroperitoneal space, and the psoas muscle to form an operative corridor to the patient's spine. For example, a K-wire or dilator may be advanced towards the surgical target site 120.

In a step 110, the K-wire and/or the neuromonitoring dilator 56 may include one or more magnetometer 32 configured to measure one or more magnetic fields propagating from stimulation of the one or more nerve stimulation electrode 18 while the K-wire and/or the dilator is being used to form the operative corridor. For example, the neuromonitoring dilator 56 having one or more magnetometer 32 may be used to measure one or more magnetic field propagating from stimulation of the nerve (e.g., femoral nerve). In some embodiments, such data may be used to provide position, orientation, and/or functionality with regard to the nerve.

During positioning of the surgical instrument 20, e.g., K-wire and/or the neuromonitoring dilator 56, the control unit 14 may monitor data provided by the one or more magnetometer 32 to determine whether the surgical instrument 20 may be interfering with any of the nerves and/or determine position and/or orientation of the nerves in relation to the surgical instrument 20. Generally, the magnetic field generated by electrical stimulation of the nerve may be measured by the one or more magnetometer 32 as the action potential of the nerve propagates through the nerve fiber. As the timing of the magnetic field may be related to the change in electrical field, measurement of the magnetic field may occur as the crest (i.e., peak) of the magnetic flux. Even further, distance to the nerve from the one or more magnetometer 32 may be determined by the amplitude of the magnetic field signal. For example, the closer to the nerve the magnetometer 32 is, the higher the amplitude signal may be. The absolute proximity threshold for detection will depend on the magnetometer sensitivity, orientation of the magnetometer 32 with the nerve axis, magnetic noise, and the amplitude of the specific nerve's action potential signal.

In some embodiments, measurements provided by multiple magnetometers 32 (e.g., 2 or more magnetometers) may be used to determine the spatial relationship of the surgical instrument 20 relative to the nerve. Measurements of the magnetic field from multiple magnetometers 32 may be used to generate a predictable three-dimensional map as a magnetic field at a given point provides both a direction and magnitude, and as such is a vector field. Combining magnetic field measurements (e.g., vector fields) from multiple magnetometers 32 provides the three-dimensional map. Such three-dimensional map may be provided to a surgeon via the output device 42.

Even further, using multiple magnetometers 32, identification of the magnetic field generated by the electrical stimulation to and from the surgical instrument 20 may be determined. Other methods of determining the spatial relationship using two or more magnetometers 32 may be used including, but not limited to, triangulation techniques.

In some embodiments, an obturator (not shown) may be included inside of the neuromonitoring dilator 56 and may similarly be equipped with one or more magnetometer 32. Once proper location is achieved, the obturator (not shown) may be removed and the K-wire inserted down the center of the neuromonitoring dilator 56 and docked to the given surgical target site 120, such as the annulus of an intervertebral disc. During a period of time in which nerve stimulation and monitoring by way of the one or more magnetometer 32, one or more additional neuromonitoring dilator 56 of increasing diameter (e.g., 6 mm to 30 mm) may then be guided over a previously installed neuromonitoring dilator 56 until a desired lumen is installed. In some embodiments, each additional neuromonitoring dilator 56 may include one or more magnetometer 32 to allow detection and direct evaluation of nerves. A working dilator (not shown) may be installed over a last one of the neuromonitoring dilator 56 and then all neuromonitoring dilators 56 removed from inside the inner lumen of the working dilator to establish the operative corridor. In some embodiments, the working dilator (not shown) may also include one or more magnetometer 32 to allow for detection and direct evaluation of the status of the nerves.

Figure 10A:
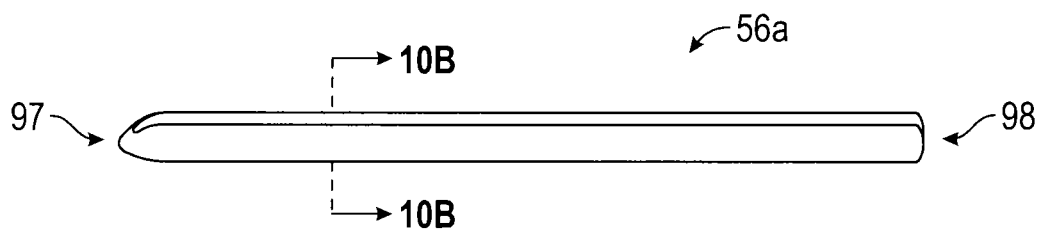
FIG. 10A is a side view of another exemplary neuromonitoring dilator for use in the intraoperative magnetometry monitoring system illustrated in FIG. 1.
Figure 10B:
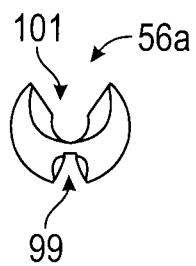
FIG. 10B is a cross sectional view taken along line 9B-9B of the neuromonitoring dilator illustrated in FIG. 10A.
Figure 10C:
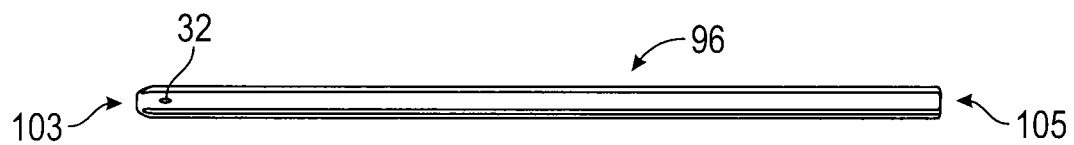
FIG. 10C is a side view of an exemplary probe for use in the neuromonitoring dilator illustrated in FIG. 10A.

In some embodiments, a separate probe having one or more magnetometers 32 may be slidably engaged with one or more neuromonitoring dilators 56. FIGS. 10A, 10B, and 10C illustrate an exemplary neuromonitoring dilator 56a configured to be slidably engaged with a probe 96 having one or more magnetometers 32 positioned thereon and/or therein. The neuromonitoring dilator 56a slidably engaged with the probe 96 may generate data indicative of magnetic fields being generated by one or more nerve so as to assist in monitoring the magnetic fields for determination of the presence and/or proximity of nerves.

The neuromonitoring dilator 56a may be of tubular construction having a first end 97 and a second end 98. The first end 97 of the neuromonitoring dilator 56a may be tapered. In some embodiments, the neuromonitoring dilator 56a may be made of a non-magnetically conductive material such as austenitic stainless steel, aluminum, biocompatible plastic or the like such that the dilator 56a does not interfere with the receipt of electromagnetic signals by the one or more magnetometers 32.

FIG. 10B illustrates a cross section of the neuromonitoring dilator 56a illustrated in FIG. 10A. The neuromonitoring dilator 56a may include one or more grooves 99 for slidably engaging the one or more probes 96. For example, in FIG.

Figure 10D:
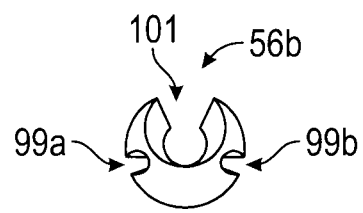
FIG. 10D is a cross sectional view of another exemplary neuromonitoring dilator for use in the intraoperative magnetometry monitoring system illustrated in FIG. 1.

10B, the neuromonitoring dilator 56*a* includes the groove 99. The one or more grooves 99 may extend between the first end 97 and the second end 98 of the neuromonitoring dilator 56*a*. Additionally, in some embodiments, the neuromonitoring dilator 56*a* may include one or more slots 101 which assists in positioning an adjacent dilator as is known in the art. FIG. 10D illustrates a cross section of another exemplary neuromonitoring dilator 56*b* wherein the neuromonitoring dilator 56*b* include a first grove 99*a* and a second grove 99*b* configured to slidably engage at least two probes 96.

FIG. 10C illustrates the probe 96 having one or more magnetometers 32. The probe 96 may have a first end 103 and a second end 105. The first end 103 may be tapered in some embodiments. One or more magnetometers 32 may be positioned on the first end 103, the second end 105, and/or between the first end 103 and the second end 105. For example, in FIG. 10C, the magnetometer 32 is positioned on the first end 103 of the probe 96 so that the magnetometer 32 is positioned adjacent to the first end 97 with the probe 96 is fully positioned within the groove 99. The probe 96 may be made of a non-magnetically conductive material such as austenitic stainless steel, aluminum, biocompatible plastic, and/or the like such that the probe 96 does not interfere with the receipt of electromagnetic signals by the one or more magnetometers 32.

Figure 6:
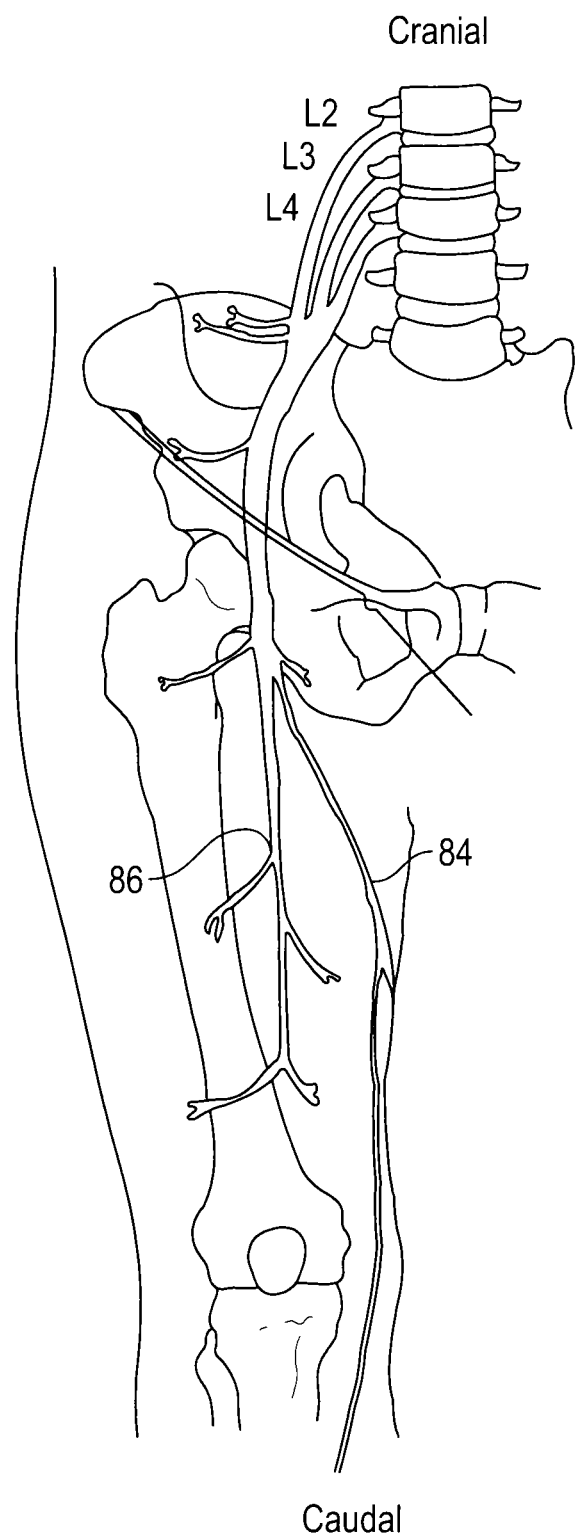
FIG. 6 is a diagrammatic view of a femoral nerve and associated branches in relation to the spinal cord.
Figure 7:
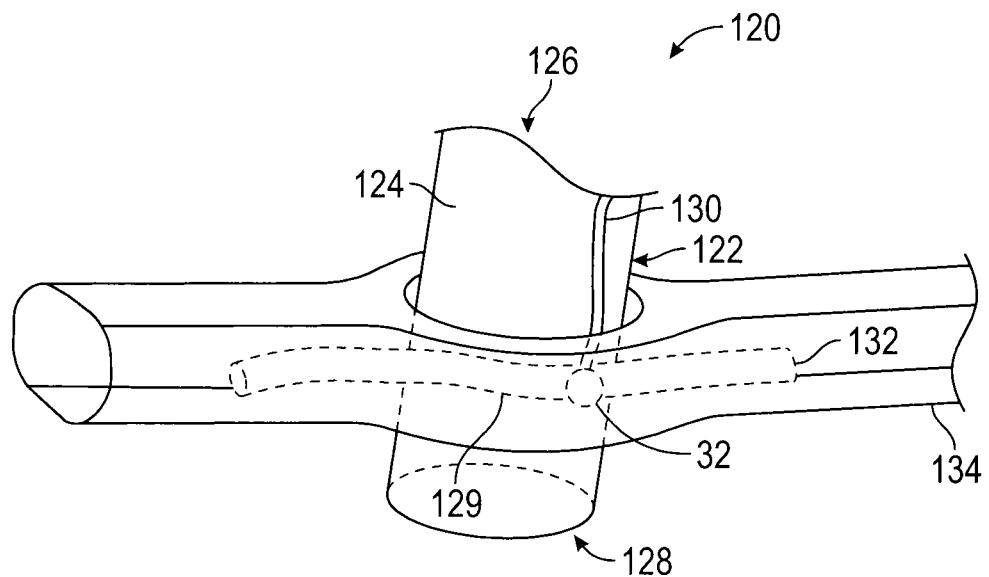
FIG. 7 is an exemplary embodiment of a surgical access instrument for use in the intraoperative magnetometry monitoring system illustrated in FIG. 1.

FIG. 6 illustrates a portion of a patient's body, and FIG. 7 illustrates an exemplary surgical access instrument 122 being used for nerve conduction velocity measurement in accordance with the present disclosure. The surgical access instrument 122 can be connected to the control unit 14 in same manner as the surgical instrument 20 shown in FIG. 1. In some embodiments, the control unit 14 may assess nerve health using nerve conduction velocity (NCV). Nerve conduction velocity is a test to determine how "fast" electrical signals may be capable of moving through a nerve at the time of testing. Generally, to determine NCV, the nerve stimulation electrodes 18 may provide an electrical impulse stimulating the nerve. The nerve's resulting magnetic field activity may be recorded by the one or more magnetometers 32. The distance between the nerve stimulation electrodes 18 and the magnetometer(s) 32, may be used to determine the speed of the signals, the direction of the signals, and/or the orientation of the signals within the body.

Generally, the monitoring system 10 may be used to produce NCV measurements within the surgical target site 120; or terminating or originating from the surgical target site 120. To produce NCV measurements in relation to the surgical target site 120, one of the surgical instruments 20 may be the surgical access instrument 122 (as shown in FIG. 7) and/or at least one nerve stimulation electrode 18 may be positioned away from the surgical target site 120 and configured to stimulate on a nerve path of a nerve (e.g., femoral nerve). The surgical access instrument 122 may include one or more body 124 having a proximal end 126, a distal end 128, and one or more magnetometer 32 on the body 124. In some embodiments, the one or more magnetometer 32 may be positioned on the cranial side of the surgical access instrument 122. Positioning at the cranial side may place the magnetometer 32 after the surgical target site 120 on a nerve path 129. One magnetometer 32 is shown in FIG. 7 by way of example, however, it should be noted that additional magnetometers 32 may be used to provide additional magnetic field measurements.

In some embodiments, the one or more magnetometer 32 may communicate with the patient module 16 via a communication link 130. The communication link 130 may be wired or wireless. For example, the communication link 130 in FIG. 7 may communicate data to the patient module 16 via a wired connection propagating from the magnetometer 32 to the proximal end 126 of the surgical access instrument 122. The surgical access instrument 122 may be in the form of a probe, dilator, retractor, or any other suitable medical instrument, for example, as long as the surgical access instrument 122 may be configured to be placed at the surgical target site 120 within the patient and at least one magnetometer 32 may be positioned near the tissue having one or more nerves.

The one or more magnetometer 32, in some embodiments, may be partially embedded within the surgical access instrument 122 such that a portion of the one or more magnetometer 32 may be exposed, may be connected via adhesive, or provided in any other suitable fashion, for example. For example, if the surgical access instrument 122 is a retractor with the body 124 having one or more blades, the one or more magnetometer 32 may be partially embedded in or placed on one of the one or more blades.

Generally, the monitoring system 10 may provide NCV measurements by placing the body 124 of the surgical access instrument 122 at the surgical target site 120 near the nerve 132. For example, the surgical target site 120 may be located close to the nerve fibers between spinal locations L-2, L-3, and L-4 illustrated in FIG. 6. It will be understood that the NCV measurements may also be used for any nerve pertinent to a surgical procedure.

The body 124 of the surgical access instrument 122 may be positioned in the tissue (e.g., psoas muscle 134), proximate to the nerve 132. The one or more nerve stimulation electrode 18 may be placed at a predetermined distance from the surgical target site 120 (e.g., anterior medial thigh between the Sartorius and Vastus medialis muscles for the saphenous nerve 84 illustrated in FIG. 6), and the body 124 of the surgical access instrument 122 along the nerve path 129 formed by the nerve 132.

The one or more nerve stimulation electrode 18 may stimulate the nerve 132 allowing for the magnetometer(s) 32 to receive magnetic field signals indicative of a neural response to the stimulation by the one or more nerve stimulation electrode 18. The monitoring system 10, as such, may be able to monitor the nerve conduction velocity of the nerve 132. Generally, a baseline NCV measurement may be taken at the beginning of the surgical procedure to establish a normal range of NCV for the patient. NCV measurements may then occur at predetermined intervals, or random intervals, during a surgical procedure to monitor nerve conduction velocity of the nerve 132.

Figure 8:
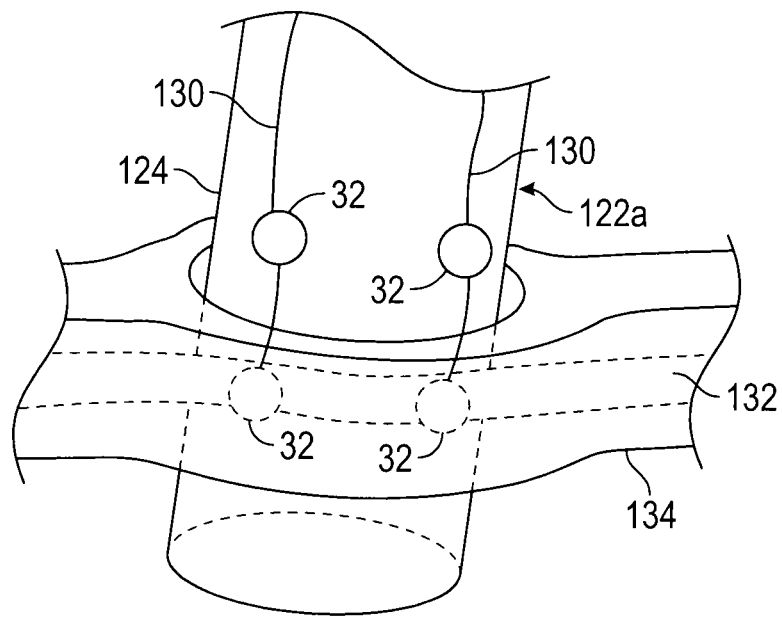
FIG. 8 is another exemplary embodiment of a surgical access instrument for use in the intraoperative magnetometry monitoring system illustrated in FIG. 1.

FIG. 8 illustrates another embodiment of a surgical access instrument 122*a* constructed in accordance with the present disclosure. The surgical access instrument 122*a* may be identical in construction and function as the surgical access instrument 122 described in FIG. 7, with the exception that the surgical access instrument 122*a* includes multiple magnetometers 32. Using multiple magnetometers 32, direction and movement of the magnetic field propagating due to stimulation of the nerve may be determined as described in further details herein. Local NCV calculations may be possible as the action potential wave moves along the nerve and different magnetometers 32 detect the maximum peak at the moment the action potential wave is closest to the magnetometers 32.

One skilled in the art will recognize that the presently disclosed concepts may be implemented in a variety of manners, such as systems, products, methods, and/or kits of component parts grouped together and/or capable of being assembled. For example, in one embodiment, the surgical access instrument 122 and/or the surgical access instrument 122a may be grouped together with the control unit 14 and/or the patient module 16 to form a surgical system kit.

Additionally, the concepts disclosed herein may be included within the system disclosed in WO2013/067018, which is incorporated by reference in its entirety. For example, one or more surgical instrument 20 having one or more magnetometer 32 may be used in the neurophysiological monitoring system as a surgical accessory as described in WO2013/067018.

The preceding description has been presented with reference to some embodiments. Persons skilled in the art and technology to which this disclosure pertains will appreciate that alterations and changes in the described structures and methods of operation may be practiced without meaningfully departing from the principle, and scope of this application. Accordingly, the foregoing description should not be read as pertaining only to the precise structures described and shown in the accompanying drawings, but rather should be read as consistent with and as support for the following claims.

Furthermore, none of the description in the present application should be read as implying that any particular element, step or function is an essential element which must be included in the claim scope. The scope of the patented subject matter is defined only by the allowed claims. Moreover, none of these claims are intended to invoke paragraph six of 35 U.S.C. § 112 unless the exact words "means for" are followed by a participle.

What is claimed is:

1. A neurophysiological monitoring system, comprising:
    at least one surgical instrument including at least one magnetometer;
    at least one nerve stimulation electrode separate from the at least one surgical instrument and configured to be positionable away from a surgical target site and activated to provide stimulation to a nerve;
    at least one control unit having one or more processor coupled to one or more memories and configured to receive magnetic field data generated by the at least one magnetometer, the one or more memories being non-transitory memory; and,
    processor executable code stored on the one or more memories of the at least one control unit that when executed by the one or more processor causes the one or more processor to:
        provide stimulation to the nerve at a known stimulation time by activating the at least one nerve stimulation electrode;
        receive magnetic field data from the at least one magnetometer indicative of a response to stimulation of the nerve at a receive time;
        generate an interpretation of the magnetic field data based upon the receive time along with the stimulation time; and,
        output information indicative of the interpretation.

2. The neurophysiological monitoring system of claim 1, wherein interpretation of the magnetic field data includes formation of a three-dimensional map of the magnetic field.

3. The neurophysiological monitoring system of claim 1, wherein interpretation of the magnetic field data includes determination of nerve conduction velocity.

4. The neurophysiological monitoring system of claim 1, wherein at least one magnetometer is a fluxgate circuit.

5. The neurophysiological monitoring system of claim 4, wherein the surgical instrument is a probe, and the fluxgate circuit is mounted on the probe.

6. The neurophysiological monitoring system of claim 4, wherein the surgical instrument is a retractor blade, and the fluxgate circuit is mounted on the retractor blade.

7. The neurophysiological monitoring system of claim 1, wherein two or more magnetometers are positioned on orthogonal axes such that interpretation of the magnetic field data provide directional information with respect to the stimulated nerve.

8. The neurophysiological system of claim 1, wherein the magnetic field data includes amplitude of the magnetic field, and interpretation of the magnetic field further includes determining distance of the magnetometer to the nerve using amplitude of the magnetic field.

9. The neurophysiological system of claim 1, wherein the surgical instrument is a surgical access instrument having a cranial side, and the at least one magnetometer is located at the cranial side of the surgical access instrument.

10. The neurophysiological system of claim 1, further comprising a patient module, and wherein the magnetometer and the patient module communicate via a network.

11. The neurophysiological system of claim 1, wherein the control unit further includes an input device and an output device, the input device and the output device including a touch screen display, and outputting information indicative of the interpretation is defined further as displaying the information on the touch screen display.

12. One or more non-transitory memory storing processor executable code that when executed by one or more processors cause the one or more processors to:
    activate at least one nerve stimulation electrode to stimulate a patient's nerve at a known stimulation time, the at least one nerve stimulation electrode being separate from a surgical instrument;
    receive signal data from at least one magnetometer included in the surgical instrument, the signal data indicative of a response of the patient's nerve to stimulation, the signal data including magnetic field data and a receive time;
    assess the signal data and known stimulation time to obtain a nerve conduction velocity, the nerve conduction velocity being used to assess nerve health and orientation of the patient's nerve; and,
    output information indicative of the nerve health and orientation of the patient's nerve.

13. The one or more non-transitory memory of claim 12, wherein the processor executable code is configured to interpret the magnetic field data by causing the one or more processor to record at least one baseline of nerve conduction velocity of the patient's nerve.

14. The one or more non-transitory memory of claim 12, wherein the processor executable code further causes the one or more processor to display information indicating a direction and proximity of the patient's nerve based on the magnetic field data.

15. A surgical system kit, comprising:
    a surgical instrument having one or more magnetometers;
    one or more nerve stimulation electrodes separate from the surgical instrument and configured to be positionable a predetermined distance away from a surgical target site and activated to provide stimulation to a nerve; and,
    a control unit configured to be in communication with the one or more magnetometers and the one or more nerve stimulation electrodes, the control unit having one or more processor coupled to one or more non-transitory memories storing processor executable code that when executed by the one or more processors causes the control unit to provide stimulation to the nerve at a known stimulation time by activating the one or more nerve stimulation electrodes, receive information indicative of a magnetic field measured by the one or more magnetometers, and interpret the information according to nerve conduction velocity to determine a nerve conduction velocity of at least a segment of the nerve.

16. The surgical system kit of claim 15, wherein the control unit further includes an output device displaying indicia indicative of the nerve conduction velocity.

17. The surgical system kit of claim 15, wherein the surgical instrument includes a plurality of magnetometers orientated at orthogonal axes.

* * * * *